United States Patent [19]

Crock et al.

[11] 3,997,138
[45] Dec. 14, 1976

[54] SECURING DEVICES AND STRUCTURES

[76] Inventors: Henry Vernon Crock; Ljubomir Pericic, both of 2 Collins St., Melbourne, Victoria, Australia, 3000

[22] Filed: June 16, 1975

[21] Appl. No.: 587,412

[52] U.S. Cl. ............................ 248/67.5; 128/92 B; 248/68 CB; 248/71

[51] Int. Cl.² .......................................... A61F 5/01

[58] Field of Search ............... 248/67.5, 68 CB, 71; 174/156, 157, 165; 128/92 B, 92 BB; 85/41, 42; 24/135 N

[56] References Cited

UNITED STATES PATENTS

| 254,473 | 3/1882 | Gates | 24/135 N |
|---|---|---|---|
| 579,552 | 3/1897 | Austin | 85/42 |
| 619,555 | 2/1899 | Frantz | 174/165 X |
| 664,176 | 12/1900 | Risler | 85/50 R X |
| 726,651 | 4/1903 | Cullen | 174/157 X |
| 1,750,318 | 3/1930 | Kaiser | 174/156 |
| 2,292,239 | 8/1942 | Pierce et al. | 151/37 |
| 2,952,254 | 9/1960 | Keating | 128/92 BB |
| 3,552,257 | 1/1971 | Tanabe | 85/50 R X |

FOREIGN PATENTS OR APPLICATIONS 760,533  10/1956  United Kingdom ............. 248/67.5

*Primary Examiner*—Roy D. Frazier
*Assistant Examiner*—Rodney H. Bonck

[57] ABSTRACT

This invention relates to a securing device specifically having application in correcting certain forms of physical deformity and in other surgical techniques. The device includes a screw threaded component and a releasable clamping member carried by the component for releasably securing an elongated member to said component.

3 Claims, 7 Drawing Figures

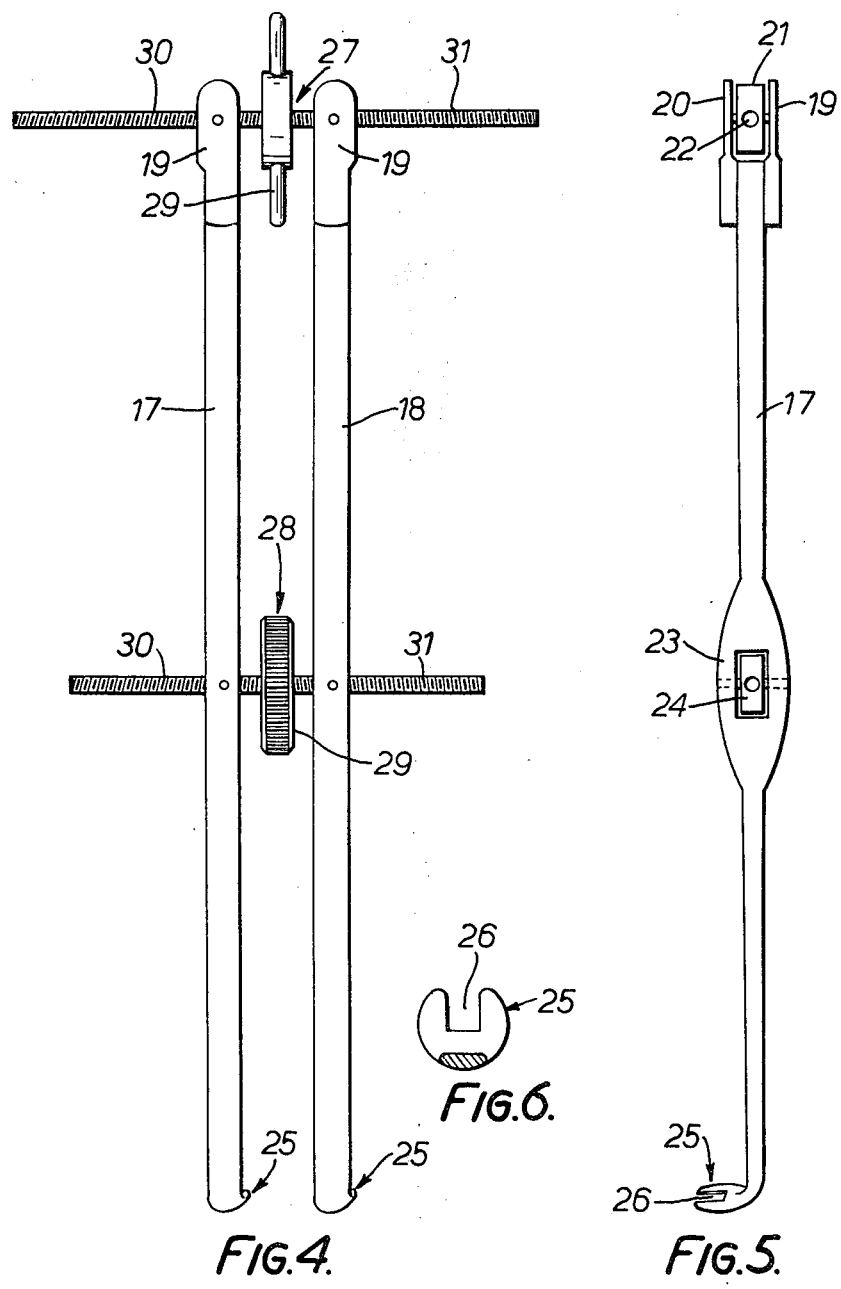

SECURING DEVICES AND STRUCTURES

This invention relates to securing devices and structures. Such devices and structures have application in correcting certain forms of physical deformity and in other surgical techniques. The devices and structures may have other applications, for example in building construction and associated fields.

For the correction of certain forms of deformity of the spine, it has been proposed to employ screws which have heads adapted to be crimped to a cable. The screws are screwed into selected vertebrae and one end of the cable is secured by crimping to the first of the screws. The cable is then tensioned by a requisite amount and then crimped to the screw immediately adjacent the first screw and this process is repeated until the cable has been crimped to all the screws. Such a technique is not entirely satisfactory. Once a screw has been crimped to the cable the connection cannot be released and the cable re-adjusted. This means that, if the deformity has been over-corrected at the time of crimping a particular screw, re-adjustment to full correction as opposed to over-correction is no longer possible.

According to the present invention, a securing device comprises a screw-threaded component and a releasable clamping member carried by the component and adapted to allow an elongated member to be releasably secured to the component.

Where the device is to be used for the correction of physical deformities and in surgical techniques, the component is screw-threaded in such manner that it can be screwed into bone structure. The form of the component and the screw-thread will be determined by the characteristics of the bone structure. Thus, for cortical bone, a self-tapping type shallow screw-thread of relatively small pitch is used to provide a reliable connection to the bone structure with minimal risk of damage to the latter. On the other hand, cancellous bone requires a screw of much larger diameter with a deep thread of a relatively coarse pitch.

In one embodiment of the invention, the component terminates in a face lying in a plane normal to the longitudinal axis of the component, there being at least one groove in the face. Extending from the face and lying along the longitudinal axis of the component is a boss on which is located a member having one or more grooves positioned to co-operate with the groove or grooves in the face. The member is movable on the boss and can be releasably secured to the latter in a desired position. Preferably, the boss is screw-threaded to receive a locking nut which is screwable along the boss to close the member towards the face.

The screw-threaded component may be integral with the boss or the latter may be separate and secured to the component once the latter has been located in a required position. In either case, the face mentioned above may also be formed on a separate member and located over the boss. The screw-threaded component may be formed with "flats" to enable it to be screwed into position with socket or other form of spanner.

The elongated member may be a rod, or a cable which may be a single or multi-strand construction.

By way of example only, an embodiment of the invention suitable for use in surgical techniques will now be described in greater detail with reference to the accompanying drawings of which:

FIG. 4 is a view from above of a compression-distraction tool,

FIG. 5 is a side view of a part of the tool shown in FIG. 4, and

FIG. 6 is an end view of another part of the tool shown in FIG. 4.

Figure 1:
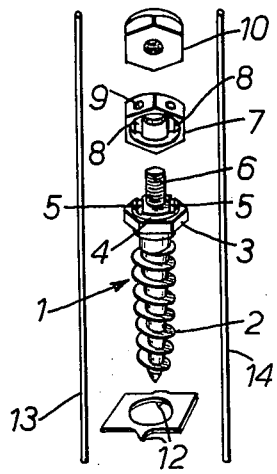
FIG. 1 is a perspective view of the components of the embodiment.
Figure 2:
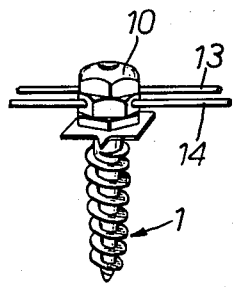
FIG. 2 is a perspective view of the components in assembled form.

The embodiment shown in FIG. 1 is suitable for use with cancellous bone and comprises a component 1 screw-threaded over the greater part of its length as indicated at 2, the thread being deep and of relatively coarse pitch. Integral with the shaft of the component 1 is a hexagonal head 3. The head 3 has a central cylindrical boss 4 across the end face of which are two channels 5 each having a cross section in a plane transverse to its length that is approximately semi-circular. The channels 5 are parallel to one another and lie along chords of the circular face of the boss 4. The boss 4 has a central screw-threaded extension 6.

A clamping member 7 in the form of a hexagonal nut is hollowed-out to fit over the boss 4 and the internal face has two channels 8 positioned and contoured to co-operate with the channels 5. Opposed side edges of the clamping member 7 have orifices 9 which allow access to the channels 5.

To secure the clamping member 7 in position, there is a lock-nut 10 that can be screwed-over the extension 6.

To provide greater stability in cancellous bones, there is provided a square washer 11 from two of whose sides extend down-turned, short prongs 12.

The boss 4 and clamping member 7 are designed to grip between them two rods parts only of which are shown in FIG. 1 at 13 and 14. The lengths of the rods will be determined by the particular application.

In its surgical application, the components just described are made of a material compatible with living tissue and bone, for example surgical grade stainless steel or titanium.

Figure 3A:
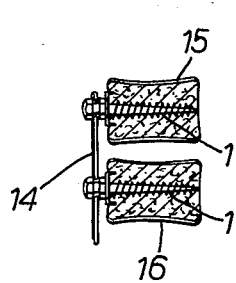
FIGS. 3A, 3B and 3C are views illustrating the use of the embodiment.
Figure 3B:
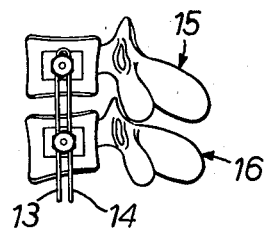
Figure 3C:
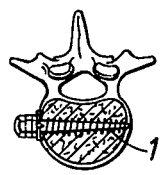

The components described are suitable for the correction of suitable forms of human spinal deformities and FIGS. 3A, 3B and 3C show the mode of use.

Components 1 with attached washers 11 are screwed into selected vertebrae — shown at 15 and 16 — until the washers have seated on the surface of the bone with the prongs 12 engaged therein. A surgical grade driver with a hollow end adapted to engage the heads 3 is used to screw the components 1 into the bones and to align the grooves 5 on the bosses 4. Rods are then passed through the orifices 9 on a series of clamping members which are then placed over the extensions 6 on the respective components 1 so that the rods are located in the passages formed by the cooperating channels in the bosses and the clamping members. Lock nuts 10 are then screwed on to the extensions 6 to hold the clamping members against the bosses but the nuts are not tightened except for the lock nut of the component 1 at one end of the series of components 1. That component may be the uppermost of the two shown in FIGS. 3A and 3B.

Using a special calliper shortly to be described, the distance between the two adjacent components 1 shown in FIGS. 3A and 3B is adjusted and then the lock nut of the lower component 1 is tightened. This process is repeated to adjust the distance between adjacent components until a desired degree of correction of the spinal deformity has been achieved.

If, at any stage, it appears that there is a risk of overcorrecting the deformity, the lock nuts of a selected component or components can be slackened to an extent sufficient to release the clamping of the rods and the contour of the spine adjusted as required after which the lock nuts are re-tightened.

Correction of the deformity may require an increase or a decrease in the distance between adjacent components and the calliper is designed to effect controlled movement of adjacent vertebrae in both directions.

It will be understood that where tension is to be applied it may be possible to use cables instead of rods.

The components and the cables or rods can thus be used in the manner described above to correct the spinal conditions known as scoliosis and kyphosis.

However, the apparatus can also be used in other surgical techniques.

For example, the apparatus can be used in the treatment of broken limb bones especially multiple breakage of the lower limb bones to maintain the length of the limb and to reduce the risk of the limb developing angularity. Components of the form described above can readily be inserted into the appropriate bones to receive one or more rods. The technique reduces the degree of trauma to which the patient is subjected and it minimises further tissue damage and interference with blood supply as compared with conventional bone fixation methods, for example bone plating.

The components and cables or rods can also be used in a variety of other surgical techniques. For example, it may be used to draw together parts of the sternum during closure of the chest following division of the sternum for operations on the thoracic contents.

It may also find application in the treatment of fractures especially in osteoporotic bones and following certain dislocations for example diastasis of the pubic symphysics.

Non-surgical applications of devices embodying the invention occur in building construction where the devices may be secured to parts of the structure of the building and used to carry rods or cables which in turn may support partitions. If rods are used, the partition may have semi-circular end surfaces contoured to fit snugly against a rod. Alternatively, the rod may be passed through a channel in the partition and be located at each end in a securing device. The rods may be either horizontal or vertical.

Alternatively, two adjacent rods may be used to support partitions which carry small projections that are engaged between the two rods. The projections are formed to facilitate insertion between the rods and to resist withdrawal therefrom.

The two-rod structure may also be used to support articles for example paintings, photographs or similar flat items on a wall. The location of the article can readily be changed merely by sliding them along the rods. Once the latter have been correctly positioned, each article can be suspended from, secured to or otherwise mounted upon the rods. The structure has advantage in picture galleries where the positions of pictures or photographs on display may be changed from time to time.

The embodiment described above employs hexagonal heads, clamping members and lock nuts. That is not essential and those articles could be square. Equally, the washers may have prongs at each corner instead of prongs on opposite sides as described above.

Conveniently, adjustment of the separation between adjacent components especially in surgical procedures may be effected using the calliper shown in FIGS. 4, 5 and 6 of the drawings.

The calliper comprises two similar levers 17, 18, each of which has extensions 19, 20 at one end which provide a mounting for a nut 21 with a screw-threaded bore 22. The nut is pivotally mounted between the extensions 19, 20 by means of short stub axles which extend from opposite faces of the nut.

About midway between its ends, each lever has an enlarged portion 23 apertures to receive a second nut 24 similar to the nut 5 and also pivotally mounted between opposite walls of the aperture.

At its other end, each lever has a fixed jaw-like extension 25 lying in a plane normal to that containing the length of the level. Each extension 25 has an opening 26 whose function will be described later.

The levers are coupled together by two adjustors 27 and 28 each comprising threaded rods extending from a central adjusting member which may take the form of short arms 29 as shown or a knurled wheel. The rods have sections 30, 31 with threads of opposite hands.

Thus, the relative positions of the levers 17, 18 can be adjusted by rotating one or both of the adjustors. For example, rotation of the adjustor 27 only will cause the levers to pivot about the nuts 23 and the ends of the levers carrying the extensions 25 will move closer together or further apart depending upon the direction of rotation of the adjustor 27. Similarly, rotation of the adjustor 28 only will cause the levers to pivot about the nuts 21. Synchronised rotation of both adjustors will cause parallel movement of the levers 17, 18 apart or together.

To use the callipers, adjustors 27 and 28 are rotated to allow the openings 26 on the extensions 25 to engage the heads 3 of adjacent components 1 after which one or other of the adjustors 27, 28 is rotated to impart a desired separation to the adjacent components.

It will be understood that it is not essential that both extensions 25 be formed with openings 26 as described above. One of the extensions may have simply a finger which can be brought into engagement with one side or the other of one of the heads of a component 1 depending upon whether that component and an adjacent component are to be moved together or further apart. The formation of one of the extensions in the manner described above facilitates location of the calliper and a more positive engagement with one of the two components.

In addition, it is not essential that the rods have two screw-threaded sections. Each rod may have a single threaded section only, being rotatably mounted at one end in the nut on one lever with the section in screw threaded engagement with the nut on the other lever.

The levers or knurled wheels used to rotate the adjustors can, if desired, be located at one end of a screw-threaded section or at the end of the one screw-threaded section if only one section is used.

We claim:

1. A securing device comprising a component having at one end a tapered screw for insertion into an element and at its other end a releasable clamping assembly for allowing an elongated member to be releasably secured to the component, said assembly including a boss having a first upper surface on the component and a movable hollow member having a second surface facing said first upper surface, said surfaces having aligned grooves for receiving the elongated member, said movable member having side walls depending from said second surface and surrounding said boss and having apertures aligned with said grooves for permitting entry of the elongated member into said grooves, and means in said assembly for securing said member to the component.

2. A device as claimed in claim 1 in which said means for securing comprises a screw threaded extension at said boss.

3. A device as claimed in claim 2 in which said assembly includes a nut for mesh engagement with the screw threaded extension, said member being clamped against the boss by means of said nut screwed on to the extension.

* * * * *